US010232162B2

(12) United States Patent
Ueda

(10) Patent No.: US 10,232,162 B2
(45) Date of Patent: Mar. 19, 2019

(54) CONNECTOR

(71) Applicant: TERUMO KABUSHIKI KAISHA, Shibuya-ku, Tokyo (JP)

(72) Inventor: Yasuhiro Ueda, Kofu (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 673 days.

(21) Appl. No.: 14/872,994

(22) Filed: Oct. 1, 2015

(65) Prior Publication Data

US 2016/0022978 A1 Jan. 28, 2016

Related U.S. Application Data

(63) Continuation of application No. PCT/JP2013/002249, filed on Apr. 1, 2013.

(51) Int. Cl.
*A61M 39/10* (2006.01)
*A61M 39/24* (2006.01)
(Continued)

(52) U.S. Cl.
CPC ......... *A61M 39/105* (2013.01); *A61M 39/286* (2013.01); *A61M 2039/0072* (2013.01); (Continued)

(58) Field of Classification Search
CPC ........ A61M 39/105; A61M 2039/1072; A61M 2039/2426; A61M 39/286;
(Continued)

(56) References Cited

U.S. PATENT DOCUMENTS

2009/0232586 A1 9/2009 Diodati et al.
2010/0024818 A1* 2/2010 Stenzler ............ A61M 16/0463
128/204.18
(Continued)

FOREIGN PATENT DOCUMENTS

JP 2000-217929 A 8/2000
JP 2010-075684 A 4/2010
(Continued)

OTHER PUBLICATIONS

Extended European Search Report dated Sep. 23, 2016 in counterpart European Application No. 13 881 433.0 (9 pages, in English).
(Continued)

*Primary Examiner* — Theodore Stigell
(74) *Attorney, Agent, or Firm* — Buchanan Ingersoll & Rooney PC

(57) ABSTRACT

A connector includes a connector main body having a flow path, an insertion body having a tip serving as a connection opening for the flow path, a valve body formed of an elastic body and arranged on the tip of the insertion body to block the connection opening, and a cap which holds the valve body together with the insertion body. The valve body includes a valve main body having slits, an inner projection formed in an annular shape having an outer diameter smaller than the inner diameter of the insertion body and projecting from a bottom face of the valve main body, and a pair of outer projections arranged point-symmetrically to each other with respect to the axis of the inner projection, each of the pair of outer projections projecting from the bottom face on the outer side in the radial direction with respect to the inner projection and being arranged on the inner side of the insertion body.

20 Claims, 7 Drawing Sheets

(51) Int. Cl.
    *A61M 39/28*     (2006.01)
    *A61M 39/00*     (2006.01)
(52) U.S. Cl.
    CPC .............. *A61M 2039/1072* (2013.01); *A61M 2039/1083* (2013.01); *A61M 2039/1088* (2013.01); *A61M 2039/2426* (2013.01)
(58) Field of Classification Search
    CPC .. A61M 2039/0072; A61M 2039/1083; A61M 2039/1088
    See application file for complete search history.

(56)             References Cited

U.S. PATENT DOCUMENTS

2011/0160679 A1   6/2011   Okiyama et al.
2011/0233435 A1   9/2011   Matsumoto et al.

FOREIGN PATENT DOCUMENTS

JP          2010-167202 A     8/2010
WO          2008043069 A2     4/2008
WO     WO 2010/073643 A1      7/2010
WO          2010110140 A1     9/2010

OTHER PUBLICATIONS

International Search Report (PCT/ISA/210) dated Jun. 18, 2013, by the Japanese Patent Office as the International Searching Authority for International Application No. PCT/JP2013/002249.

* cited by examiner

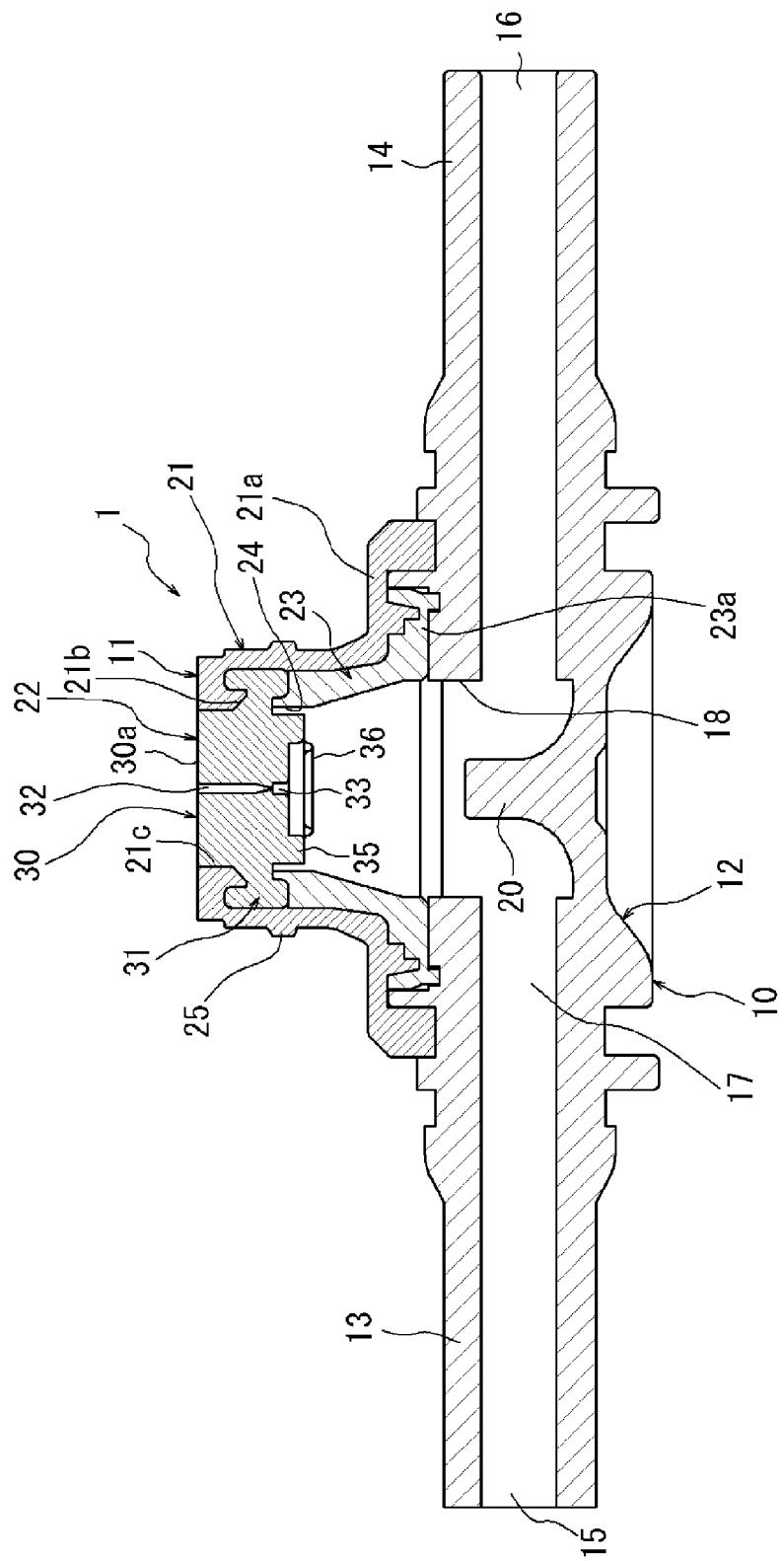

III-III CROSS SECTION

IV-IV CROSS SECTION

CONNECTOR

CROSS-REFERENCE TO RELATED APPLICATION

This application is a continuation of International Application No. PCT/JP2013/002249 filed on Apr. 1, 2013, the entire content of which is incorporated herein by reference.

TECHNICAL FIELD

The disclosure herein relates to a connector that is disposed on, for example, an infusion line to enable a member, such as another infusion line and various medical devices, to be connected to the infusion line.

BACKGROUND ART

When infusion, blood transfusion, or artificial dialysis is performed, liquid such as a liquid medicine and blood is fed into the body through an infusion line provided with a medical tube. A connector is disposed on such an infusion line, and a member, such as another infusion line and various medical devices, can be connected to the connector to join liquid such as another liquid medicine to liquid flowing inside the tube.

As such a connector, there is known a connector having a structure that includes a connector main body having a flow path, a connection opening which is formed on the connector main body and connected to a midway part of the flow path, and a disc-like valve body which is formed of an elastic body such as rubber and attached to the connection opening as described, for example, in JP 2010-167202 A. In a connector described in JP 2010-167202 A, a valve body is arranged on the tip of a cylindrical section which forms a connection opening and held by a cap (fixation member) together with the cylindrical section. A slit is formed on the valve body. A male connector disposed on a member to be connected is inserted into the slit to thereby connect the member to the connection opening.

In the above conventional connector, an annular projection which surrounds the slit is integrally formed with the bottom face of the valve body to prevent the valve body from splitting from both ends in the longitudinal direction of the slit when a male connector is inserted.

However, in the conventional connector, the outer diameter dimension of the annular projection is set smaller than the inner diameter dimension of the cylindrical section to form a gap between the outer peripheral face of the annular projection and the inner peripheral face of the cylindrical section to improve the insertability of the male connector into the valve body. Thus, when the valve body is attached to the tip of the cylindrical section in the manufacturing process of the connector, the valve body is in an unstable state that easily causes position shift in the radial direction with respect to the cylindrical section. Thus, the operability is low.

On the other hand, the valve body can be positioned in the radial direction by the annular projection and thereby stably attached to the cylindrical section by setting the outer diameter dimension of the annular projection of the valve body substantially equal to the inner diameter dimension of the connection opening of a holder. However, in such a configuration, since the outer peripheral face of the annular projection abuts against the inner peripheral face of the cylindrical section, it becomes difficult for the valve body to elastically deform. Accordingly, the insertability of the male connector is deteriorated.

SUMMARY

The disclosure herein provides a connector that makes it possible to improve the assemblability of a valve body while maintaining the insertability of a male connector to the valve body.

A connector according to an exemplary embodiment of the disclosure includes a connector main body having a flow path, a cylindrical section having an axial end that serves as a connection opening for the flow path, a valve body formed of an elastic body and arranged on the axial end of the cylindrical section to block the connection opening, and a fixation member holding the valve body together with the cylindrical section. The valve body includes a valve main body having a slit, an inner projection formed in an annular shape having an outer diameter smaller than an inner diameter of the cylindrical section, the inner projection projecting from a bottom face of the valve main body, and a pair of outer projections arranged point-symmetrically to each other with respect to an axis of the inner projection, each of the pair of outer projections projecting from the bottom face on an outer side in a radial direction with respect to the inner projection and being arranged on an inner side of the cylindrical section.

In the above configuration, the pair of outer projections is preferably arranged along a longitudinal direction of the slit.

In the above configuration, each of the pair of outer projections has an outer face, the outer faces facing outward in the radial direction, and the outer faces are preferably inclined in a direction approaching the axis of the inner projection as separating from the bottom face.

In the above configuration, a projecting height of the pair of outer projections from the bottom face is preferably larger than a projecting height of the inner projection from the bottom face.

In the disclosure herein, the annular inner projection having an outer diameter smaller than the inner diameter of the cylindrical section is formed on the bottom face of the valve main body. Further, the pair of outer projections, which are arranged point-symmetrically to each other with respect to the axis of the inner projection, each of the pair of outer projections projecting from the bottom face of the valve main body on the outer side in the radial direction with respect to the inner projection and being arranged on the inner side of the cylindrical section, are formed on the bottom face of the valve main body. Accordingly, when the valve body is arranged on the end of the cylindrical section in the manufacturing process of the connector, the valve body can be positioned in the radial direction with respect to the cylindrical section by the pair of outer projections. Thus, it is possible to stabilize the valve body arranged on the end of the cylindrical section to improve the assemblability of the valve body to the connector main body. Further, since the pair of outer projections is arranged point-symmetrically to each other with respect to the axis of the inner projection, an escape space for the valve body can be ensured in a part in which the pair of outer projections is not formed. Therefore, when a male connector is inserted into the valve body, it is possible to allow the valve body to elastically deform toward the escape space in which the pair of outer projections is not formed to improve the insertability of the male connector into the valve body. In this manner, the disclosure provides a connector that makes it possible to improve the assemblability of the valve body while maintaining the insertability of the male connector into the valve body. Further, when the male connector is inserted into the valve body, a restoring force in a direction for closing the slit is applied to the valve body by the pair of outer projections. Thus, the restorability of the valve body to a closed state can be improved.

In the disclosure herein, the pair of outer projections is arranged along the longitudinal direction of the slit. Accordingly, when the male connector is inserted into the valve body, it is possible to prevent the pair of outer projections from obstructing opening of the slit to further improve the insertability of the male connector into the valve body.

In the disclosure herein, each of the pair of outer projections includes an outer face, the outer faces facing outward in the radial direction, are inclined in the direction approaching the axis of the inner projection as separating from the bottom face. Accordingly, it is possible to allow the pair of outer projections to be easily inserted into the inner side of the cylindrical section to further improve the assemblability of the valve body to the cylindrical section. When the valve body is assembled to the cylindrical section, a gap which gradually expands as separating from the bottom face is generated between each of the outer faces of the outer projections and the inner peripheral face of the cylindrical section. Thus, when the male connector is inserted into the valve body, it is possible to allow the pair of outer projections to easily elastically deform outward in the radial direction toward the gap. Accordingly, it is possible to further improve the insertability of the male connector into the valve body.

In the disclosure herein, the projecting height of the pair of outer projections from the bottom face is larger than the projecting height of the inner projection from the bottom face. Accordingly, it is possible to increase the volume or cross-sectional area of each of the outer projections without increasing the width dimension of each of the outer projections along the circumferential direction of the inner projection to thereby further improve the restorability of the valve body without deteriorating the insertability of the male connector into the valve body.

BRIEF DESCRIPTION OF THE DRAWINGS

FIG. 3 is sectional view of the connector illustrated in FIG. 1.

DETAILED DESCRIPTION

Figure 1:
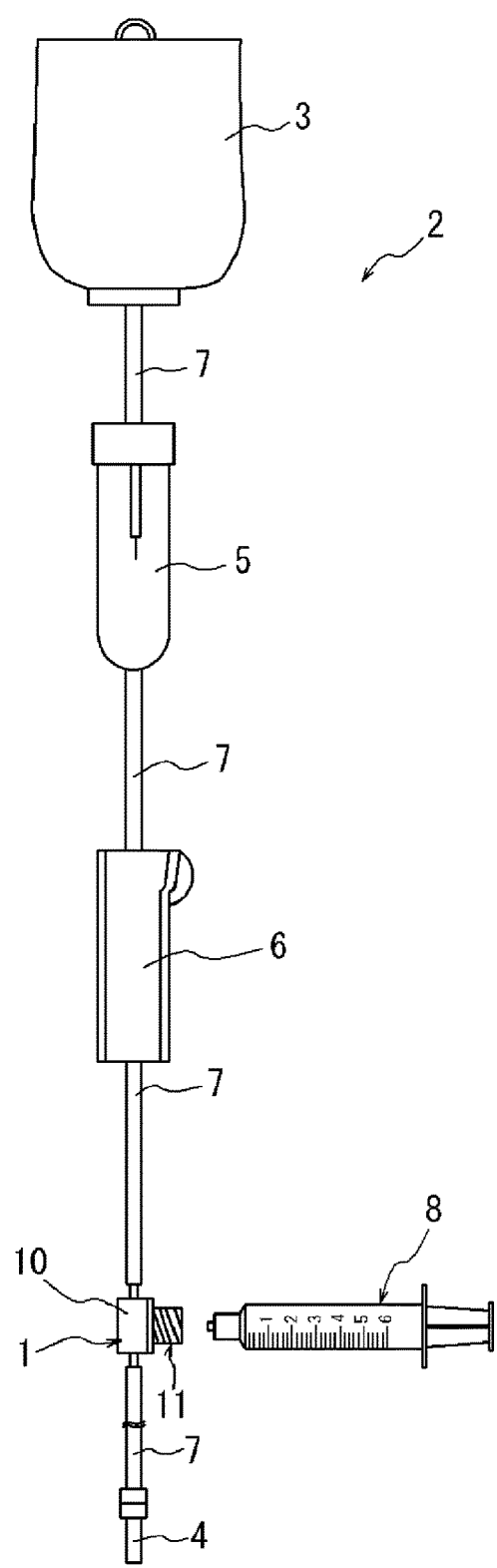
FIG. 1 is a diagram illustrating an infusion line in which a connector which is an exemplary embodiment of the disclosure is used.

As illustrated in FIG. 1, the connector 1 which is an exemplary embodiment of the disclosure is disposed on, for example, an infusion line 2. The infusion line 2 is provided with an infusion solution bag 3 which stores liquid such as a liquid medicine, an indwelling needle 4 which is inserted into, for example, the vein of a patient, a drip infusion cylinder 5, and a clamp 6, the drip infusion cylinder 5 and the clamp 6 being disposed between the infusion solution bag 3 and the indwelling needle 4. These members are connected through a medical tube 7. The connector 1 is disposed on the infusion line 2 to enable a member to be connected such as a syringe 8 to be connected to the infusion line 2.

FIG. 1 illustrates a case in which the syringe 8 is connected to the connector 1. However, not only the syringe 8, but also, for example, another medical device such as a dialyzer, another infusion line, or an extension tube may be connected to the connector 1.

Figure 2:
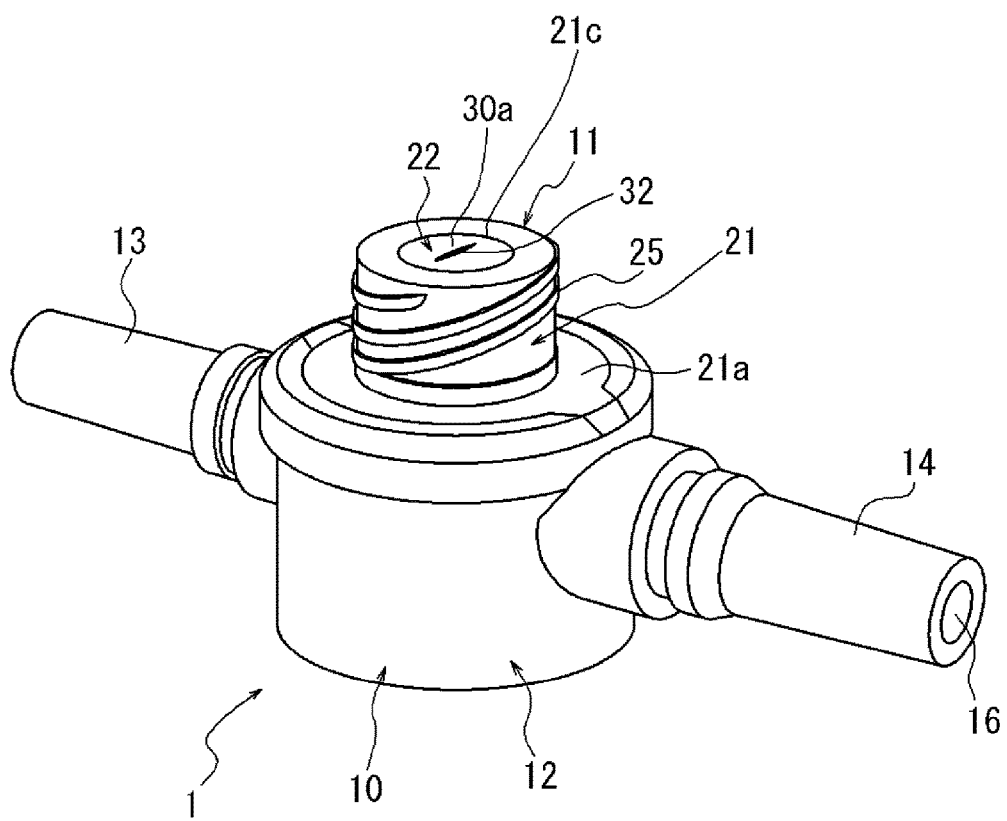
FIG. 2 is a perspective view illustrating details of the connector illustrated in FIG. 1.

As illustrated in FIGS. 2 and 3, the connector 1 includes a connector main body 10 which is also called a holder and a cap assembly 11 which is fixed to the connector main body 10.

The connector main body 10 is provided with a main body section 12 which is formed in a substantially columnar shape and a pair of connection sections 13, 14, and these members are integrally formed by injection-molding a resin material. The connector main body 10 may be formed of, for example, various metal materials, glass materials, or ceramic materials.

Each of the connection sections 13, 14 is formed in a cylindrical shape and projects outward in the radial direction from the outer peripheral face of the main body section 12. The axis of the connection section 13 and the axis of the connection section 14 are aligned with each other. These axes are also aligned with the radial direction of the main body section 12. An opening end of one of the connection sections, specifically, the connection section 13 serves as an inflow port 15. An opening end of the other connection section, specifically, the connection section 14 serves as an outflow port 16. Thus, the connector 1 can be connected to the infusion line 2 by inserting the connection section 13 into the tube 7 of the infusion line 2 at a side corresponding to the infusion solution bag 3 and inserting the connection section 14 into the tube 7 of the infusion line 2 at a side corresponding to the indwelling needle 4. Alternatively, the opening end of the connection section 13 may serve as the outflow port 16 and the opening end of the connection section 14 may serve as the inflow port 15.

As illustrated in FIG. 3, a flow path 17 which extends from the inflow port 15 of the connection section 13 up to the outflow port 16 of the connection section 14 through the inside of the main body section 12 is formed inside the connector main body 10. That is, the flow path 17 extends along the radial direction of the main body section 12 and communicates with the inflow port 15 and the outflow port 16.

An opening hole 18 is formed on one end face (a face located on the upper side in FIG. 3) of the main body section 12. The opening hole 18 is formed in a circular shape coaxial with the main body section 12 and connected to an intermediate part of the flow path 17. A projection 20 which projects from the bottom face side of the flow path 17 toward the opening hole 18 is integrally formed with the main body section 12. The flow path 17 is thus turned in a "crank" shape toward the opening hole 18 by the projection 20. More particularly, the flow path 17 is turned around the projection 20 in a series of substantially right angles between the inflow port 15 and the outflow port 16.

As illustrated in FIG. 3, the cap assembly 11 has a configuration in which a valve body 22 and an insertion body 23 having a cylindrical section are attached to the inside of a cap 21 as a fixation member. The cap assembly 11 is fixed to the end face in the axial direction of the main body section 12 of the connector main body 10 to cover the opening hole 18.

The insertion body 23 is formed in a cylindrical shape coaxial with the main body section 12 and arranged on the end face of the main body section 12 on a flange 23a which is formed on one end in the axial direction of the insertion body 23. The insertion body 23 is formed, for example, by injection-molding a resin material. Alternatively, the insertion body 23 may also be formed of another material as with the connector main body 10. The inner diameter dimension of the insertion body 23 on one end having the flange 23a is substantially equal to the inner diameter dimension of the opening hole 18. The insertion body 23 is arranged coaxially with the opening hole 18. Accordingly, one end of the insertion body 23 is connected to the opening hole 18, that is, a midway part of the flow path 17. In this manner, the insertion body 23 is disposed on the midway part of the flow path 17. The other end in the axial direction of the insertion body 23, that is, the tip facing opposite to the main body section 12 constitutes a connection opening 24 for the flow path 17 formed on the connector main body 10.

The valve body 22 is formed of, for example, an elastic body such as a rubber material and a thermoplastic elastomer and arranged on the tip (end) of the insertion body 23 to block the connection opening 24. Details of the shape of the valve body 22 will be described below.

The cap 21 is formed in a cylindrical shape and attached to the outer side of the insertion body 23 to cover the valve body 22 and the insertion body 23. The cap 21 is formed, for example, by injection-molding a resin material. Alternatively, the cap 21 may also be formed of another material as with the connector main body 10 and the insertion body 23. A flange 21a is integrally formed with the base end of the cap 21. The flange 21a is ultrasonic-welded (fused) to the main body section 12 to fix the cap 21 to the main body section 12. The cap 21 may be fixed to the main body section 12 using another fixation means such as adhesive and press-fitting instead of ultrasonic welding.

The insertion body 23 is previously inserted into the cap 21 and fixed to the main body section 12 by the flange 23a held between the flange 21a of the cap 21 and the main body section 12. The valve body 22 is previously held between the tip of the insertion body 23 and a locking section 21b formed on the end of the cap 21 and thereby held and fixed between the insertion body 23 and the cap 21. The insertion body 23 is not limited to the configuration in which the insertion body 23 is held and fixed between the cap 21 and the main body section 12 and may be directly fixed to the main body section 12 using fixation means such as ultrasonic welding and adhesive.

An external thread 25 which has a shape defined by International Organization for Standardization (ISO) standard numbers ISO 594-1 and ISO 594-2 is formed on the outer peripheral face of the cap 21. The external thread 25 is a double-start thread and can be screwed with an internal thread of a lock connector disposed on the medical syringe 8 or the like. A connection hole 21c is formed on the end of the cap 21. The valve body 22 is exposed through the connection hole 21c.

Next, details of the shape of the valve body 22 used in the connector 1 of the disclosure will be described in detail with reference to FIGS. 4 to 6.

The valve body 22 includes a valve main body 30 which is formed of, for example, an elastic body such as a rubber material and a thermoplastic elastomer in a substantially columnar shape (disc-like shape) and a held section 31.

The held section 31 is integrally formed with the outer peripheral part of the valve main body 30. The held section 31 is held between the locking section 21b formed on the cap 21 and the tip of the insertion body 23. Accordingly, the valve body 22 is held and fixed between the insertion body 23 and the cap 21.

Figure 4A:
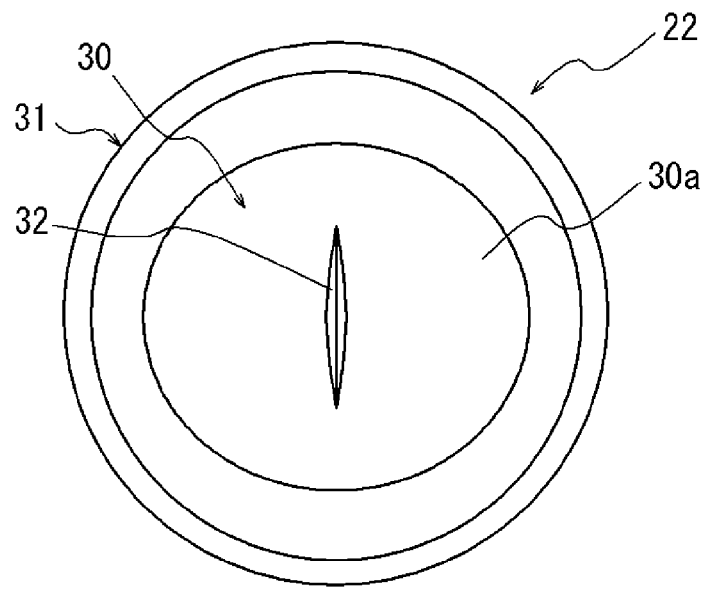
FIG. 4(A) is a plan view of a valve body illustrated in FIG. 3.
Figure 5A:
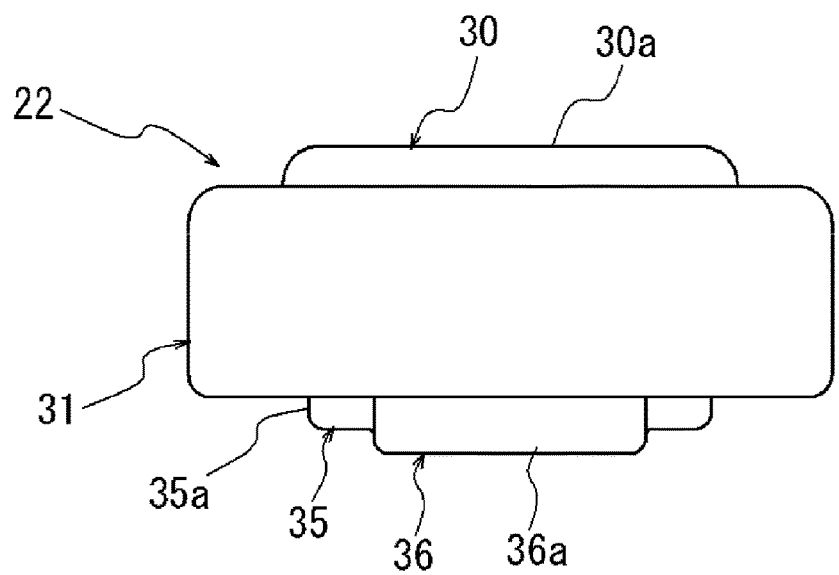
FIG. 5(A) is a diagram of the valve body illustrated in FIG. 4(B) viewed from arrow I.
Figure 5B:
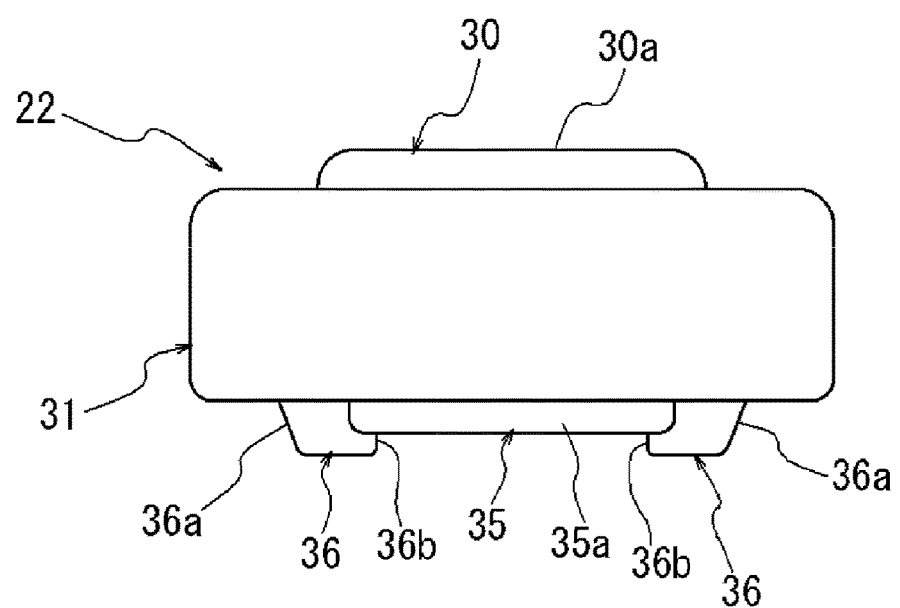
FIG. 5(B) is a diagram of the valve body illustrated in FIG. 4(B) viewed from arrow II.

An axial end face of the valve main body 30, the axial end face facing the connection hole 21c of the cap 21, constitutes a push-in face 30a. As illustrated in FIG. 4(A), a slit 32 which linearly extends along the radial direction of the valve main body 30 is formed on the center of the push-in face 30a.

The push-in face 30a is formed in an elliptical shape having a minor axis in an extending direction (longitudinal direction) of the slit 32 and a major axis in a direction perpendicular to the longitudinal direction of the slit 32 when not housed in the connection hole 21c. When the valve body 22 is housed in the connection hole 21c, the ellipse is pushed by the connection hole 21c on the major axis side thereof to form a circular shape. Accordingly, inner faces of the slit 32 are brought into intimate contact with each other to close the slit 32.

Figure 4B:
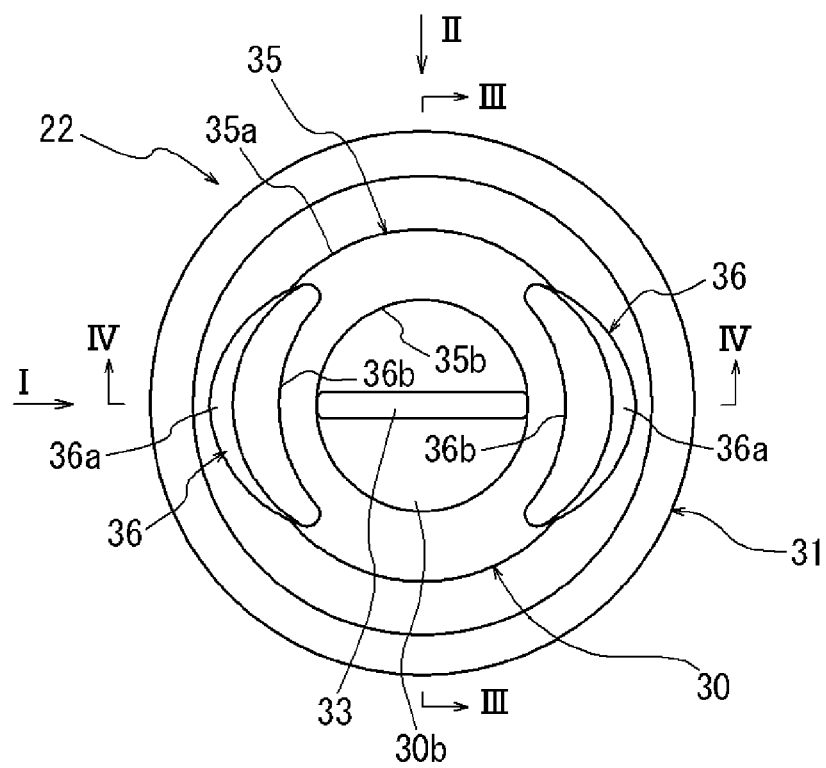
FIG. 4(B) is a bottom view of the valve body illustrated in FIG. 3.
Figure 6A:
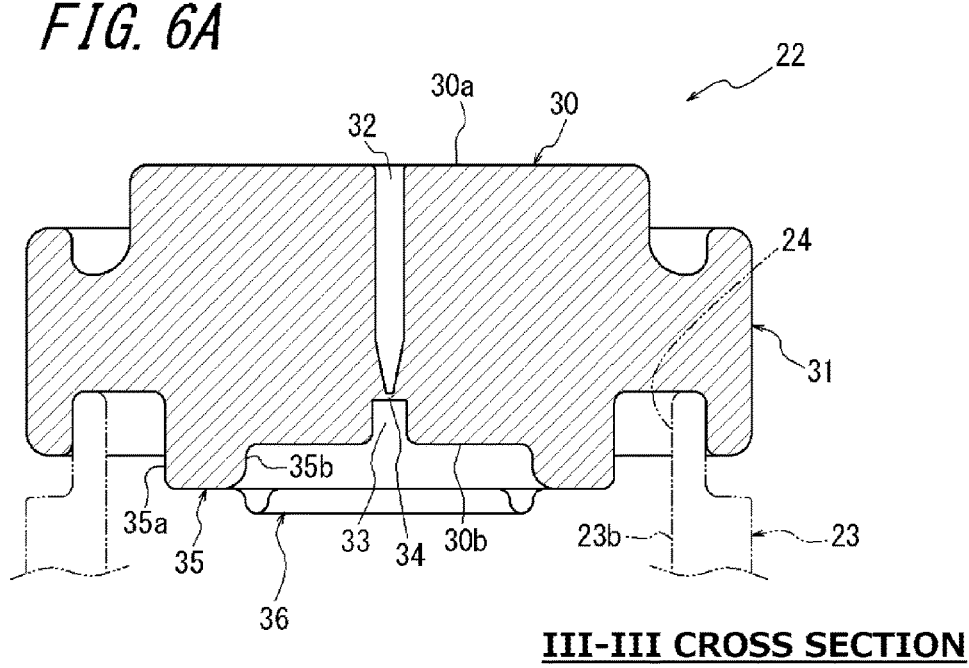
FIG. 6(A) is a sectional view taken along line III-III in FIG. 4(B)

On the other hand, as illustrated in FIG. 4(B), a sub slit (depression) 33 which linearly extends along the radial direction of the valve main body 30 is formed on the center of a bottom face 30b of the valve main body 30, the bottom face 30b facing opposite to the push-in face 30a. The sub slit 33 faces the same direction as the slit 32 formed on the push-in face 30a. As illustrated in FIG. 6A, a thin partition wall 34 is formed between the slit 32 and the sub slit 33 and broken when a male connector is inserted into the valve body 22. The bottom face 30b of the valve main body 30 faces the flow path 17, that is, the base end side of the insertion body 23 when the valve body 22 is arranged on the tip of the insertion body 23.

In order to improve the assemblability of the valve body 22 to the insertion body 23 while maintaining the insertability of a male connector into the valve body 22, an inner projection 35 and a pair of outer projections 36 are integrally formed with the bottom face 30b of the valve main body 30.

As illustrated in FIG. 4(B), the inner projection 35 is formed in an annular shape coaxial with the valve main body 30 and projects from the bottom face 30b of the valve main body 30 in the axial direction. The outer diameter of the inner projection 35 is smaller than the inner diameter of the insertion body 23. As illustrated in FIG. 6(A), when the valve body 22 is arranged on the tip of the insertion body 23, a gap is generated between the inner peripheral face 23b of the insertion body 23 and an outer peripheral face 35a of the inner projection 35 in the radial direction. The inner projection 35 surrounds the sub slit 33 and prevents the valve body 22 from splitting in the longitudinal direction from the ends of the sub slit 33 or the slit 32 when a male connector is inserted into the valve body 22.

On the other hand, as illustrated in FIG. 4(B), each of the pair of outer projections 36 is formed in a circular arc shape extending in the circumferential direction within the range of approximately 90° around the axis of the inner projection 35. Each of the pair of outer projections 36 is arranged in a manner to align a central position in the circumferential direction thereof with a straight line along the longitudinal direction of the slit 32 and the sub slit 33. That is, the pair of outer projections 36 is arranged point-symmetrically to each other with respect to the axis of the inner projection 35 along the longitudinal direction of the slit 32 and the sub slit 33. As illustrated in FIGS. 5A, 5B and 6A, 6B, a projecting height in the axial direction of each of the outer projections 36 from the bottom face 30b is larger than a projecting height in the axial direction of the inner projection 35 from the bottom face 30b.

Each of the pair of outer projections 36 projects from the bottom face 30b on the outer side in the radial direction with respect to the inner projection 35 and has an outer face 36a which faces outward in the radial direction and is arranged on the outer side in the radial direction with respect to the outer peripheral face 35a of the inner projection 35. The outer faces 36a of the outer projections 36 are curved to project outward in the radial direction and the curvature thereof is larger than the curvature of the outer peripheral face 35a of the inner projection 35. The outer faces 36a of the outer projections 36 are formed in tapered surfaces which are gradually inclined in a direction approaching the axis of the inner projection 35 as separating from the bottom face 30b. That is, the pair of outer projections 36 is formed in tapered shapes so that a distance between the outer faces 36a of the outer projections 36 is gradually reduced from the bottom face 30b toward the tip side. An inner face 36b of each of the pair of outer projections 36, the inner face 36b facing inward in the radial direction, is arranged on the inner side in the radial direction with respect to the outer peripheral face 35a of the inner projection 35 and on the outer side in the radial direction with respect to an inner peripheral face 35b of the inner projection 35. In this manner, a part of each of the pair of outer projections 36 is arranged to overlap the inner projection 35.

Figure 6B:
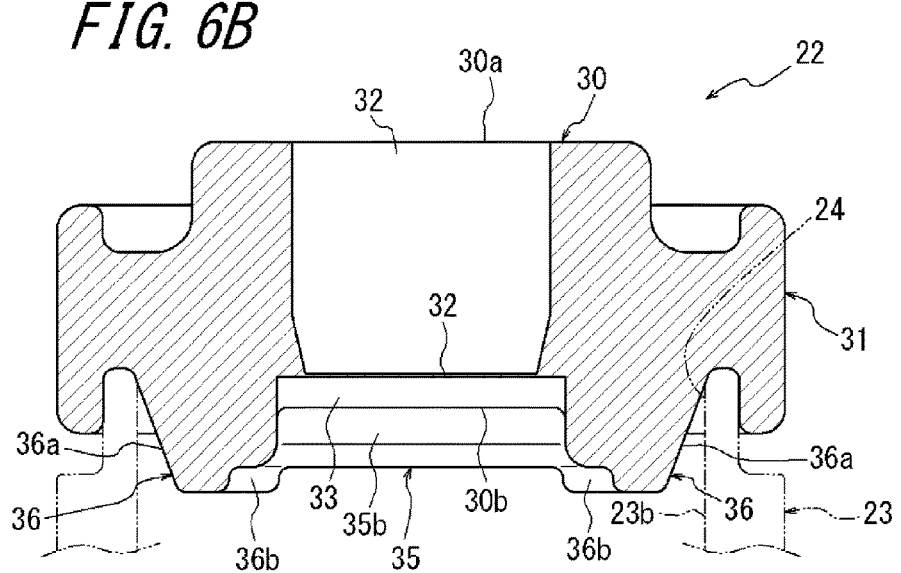
FIG. 6(B) is a sectional view taken along line IV-IV in FIG. 4(B).

A distance between the outer face 36a of one of the outer projections 36 and the outer face 36a of the other outer projection 36 on their bases connected to the bottom face 30b is set to be substantially equal to the inner diameter of the insertion body 23. Accordingly, as illustrated in FIG. 6(B), when the valve body 22 is arranged on the tip of the insertion body 23, the pair of outer projections 36 are arranged on the inner side of the insertion body 23 and the outer faces 36a of the pair of outer projections 36 come into contact with the inner peripheral face 23b of the insertion body 23 on their bases. Thus, when the valve body 22 is assembled to the tip of the insertion body 23 using the cap 21 in the manufacturing process of the connector 1, the outer faces 36a of the pair of outer projections 36 come into contact with the inner peripheral face 23b of the insertion body 23 so that the valve body 22 is positioned in the radial direction with respect to the insertion body 23 by arranging the valve body 22 on the tip of the insertion body 23. Accordingly, it is possible to stably arrange the valve body 22 on the tip of the insertion body 23 to improve the assemblability of the valve body 22 to the insertion body 23.

Each of the outer faces 36a of the pair of outer projections 36 is formed in a tapered form which is inclined in the direction approaching the axis of the inner projection 35 as separating from the bottom face 30b. Thus, it is easy to insert the outer projections 36 into the inner side of the insertion body 23 when the valve body 22 is arranged on the tip of the insertion body 23. Therefore, it is possible to further improve the assemblability of the valve body 22 to the insertion body 23.

Next, an action when a male connector is connected to the connector 1 of the disclosure will be described.

As illustrated in FIG. 3, when no male connector is connected to the connector 1, the connection opening 24 connected to the flow path 17 is blocked by the valve body 22. Thus, the connector 1 can allow liquid flowing from the infusion line 2 to flow out from the outflow port 16 through the flow path 17.

Figure 7:
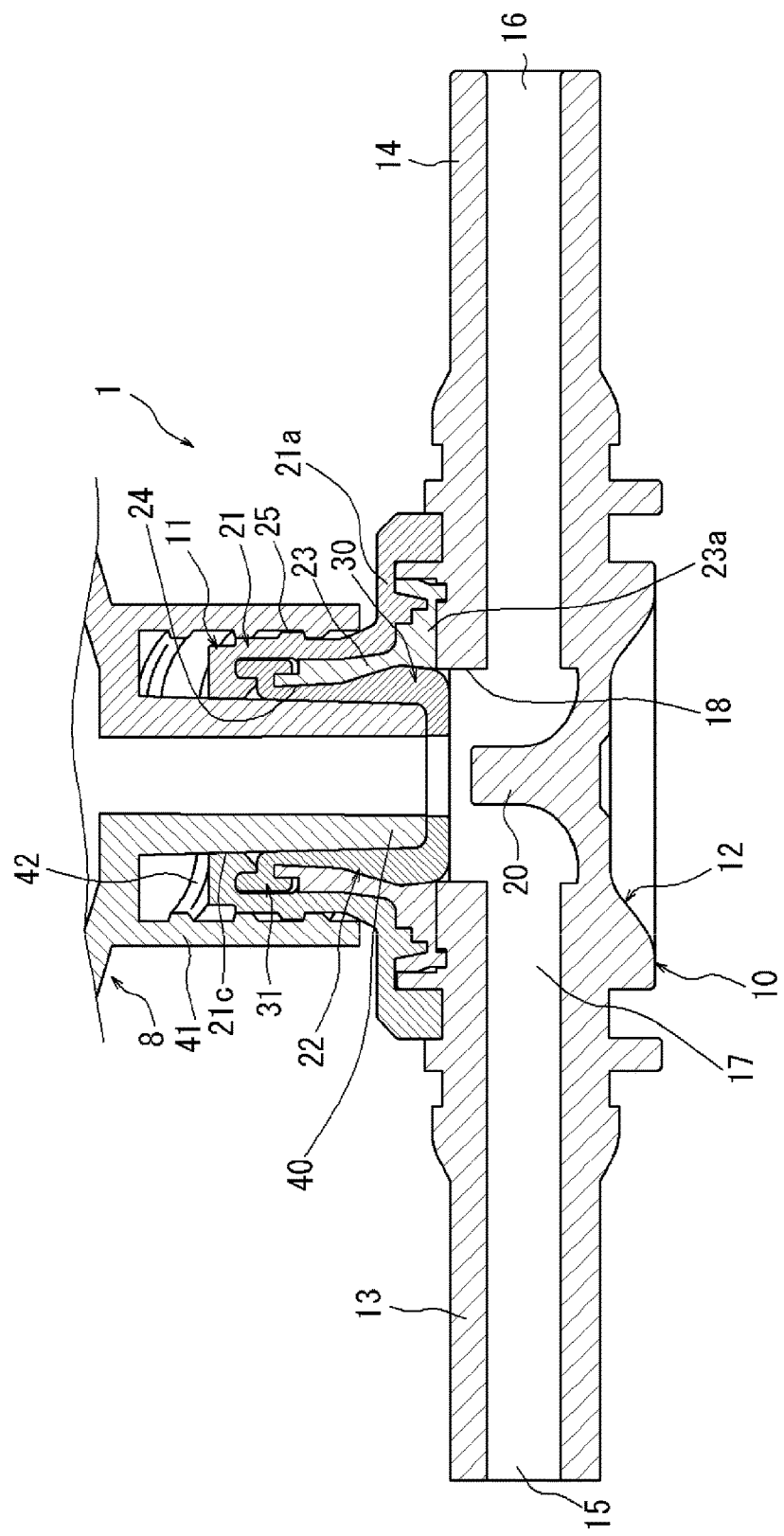
FIG. 7 is a sectional view illustrating a state in which a male connector is connected to the connector illustrated in FIG. 3.

On the other hand, a member to be connected such as the syringe 8 can be connected to the infusion line 2 through the connector 1 by inserting a male connector disposed on the member into the connector 1. FIG. 7 illustrates a state in which a male connector 40 such as a luer disposed on the syringe 8 illustrated in FIG. 1 is connected to the connector 1.

The syringe 8 has, on the tip thereof, the male connector (luer) 40 which has a shape defined by ISO standard numbers ISO 594-1 and ISO 594-2. A cylindrical barrel 41 which covers the outer side of the male connector 40 is integrally formed with the tip of the syringe 8. An internal thread 42 which has a shape corresponding to the external thread 25 of the cap 21 is integrally formed with the inner peripheral face of the barrel 41. The shape of the internal thread 42 is also defined by ISO standard numbers ISO 594-1 and ISO 594-2.

When the male connector 40 of the syringe 8 is pushed toward the slit 32 of the valve body 22, the valve body 22 elastically deforms toward the inner side of the cap 21. Accordingly, the partition wall 34 between the slit 32 and the sub slit 33 is broken to open the valve body 22. As a result, as illustrated in FIG. 7, the male connector 40 is liquid-tightly connected to the flow path 17. Further, the syringe 8 can be fixed to the connector 1 to hold the connection of the male connector 40 to the flow path 17 by screwing the internal thread 42 formed on the inner peripheral face of the barrel 41 of the syringe 8 with the external thread 25 of the cap 21.

The outer diameter of the inner projection 35 formed on the bottom face 30b of the valve main body 30 is smaller than the inner diameter of the insertion body 23. Thus, as can be understood from FIG. 6(A), when the valve body 22 is attached to the tip of the insertion body 23, a gap, that is, an escape or deformation space for the valve body 22 when elastically deforming is generated between the inner peripheral face 23b of the insertion body 23 and the outer peripheral face 35a of the inner projection 35 in a part in which the pair of outer projections 36 are not formed. Therefore, when the male connector 40 is inserted into the valve body 22, the valve body 22 can easily elastically deform toward the gap part in which the pair of outer projections 36 are not formed. Accordingly, even when the pair of outer projections 36 is formed on the bottom face 30b of the valve main body 30, the insertability of the male connector 40 into the valve body 22 can be maintained in an excellent state.

An insertion depth of the male connector 40 with respect to the valve body 22 required for connecting the male connector 40 to the flow path 17 can be reduced by allowing the valve body 22 to elastically deform toward the gap part in which the pair of outer projections 36 are not formed when the male connector 40 is inserted into the valve body 22. Accordingly, it is possible to reduce the escape space for the valve body 22 when elastically deforming inside the insertion body 23 and the connector main body 10. Reducing the escape space enables generation of a dead space which causes accumulation of liquid in the midway part of the flow path 17 to be prevented. Since the insertion depth of the male connector 40 with respect to the valve body 22 can be reduced, it is possible to reduce a change in the ejection flow amount of liquid on the indwelling needle 4 which occurs when the male connector 40 is inserted.

When the male connector 40 is inserted into the valve body 22, the pair of outer projections 36 elastically deform together with the valve main body 30, and a restoring force in a direction for closing the slits 32, 33 is applied to the valve body 22 by the elastic force of the deformation. Thus, the restorability of the valve body 22 to a closed state is improved. Accordingly, it is possible to reliably restore the valve body 22 to a closed state after the male connector 40 is removed therefrom to prevent liquid leakage from the connector 1.

The pair of outer projections 36 are arranged along the longitudinal direction of the slits 32, 33. Thus, when the male connector 40 is inserted into the valve body 22 to expand the slits 32, 33 in a direction perpendicular to the longitudinal direction thereof, the pair of outer projections 36 does not obstruct the expansion of the slits 32, 33. Therefore, arranging the pair of outer projections 36 along the longitudinal direction of the slits 32, 33 enables the insertability of the male connector 40 into the valve body 22 to be further improved.

Each of the outer faces 36a of the outer projections 36 is inclined in the direction approaching the axis of the inner projection 35 as separating from the bottom face 30b. Thus, as can be understood from FIG. 6 (B), when the valve body 22 is assembled to the tip of the insertion body 23, a gap which gradually expands in the radial direction as separating from the bottom face 30b in the axial direction is generated between each of the outer faces 36a of the outer projections 36 and the inner peripheral face 23b of the insertion body 23. Accordingly, when the male connector 40 is inserted into the valve body 22, it is possible to allow each of the pair of outer projections 36 to elastically deform toward the gap with the insertion body 23 to further improve the insertability of the male connector 40 into the valve body 22.

The projecting height of the pair of outer projections 36 from the bottom face 30b is higher than the projecting height of the inner projection 35 from the bottom face 30b. Thus, it is possible to increase the cross-sectional area of each of the outer projections 36 while maintaining a constant width dimension of each of the outer projections 36 along the circumferential direction of the inner projection 35. Accordingly, it is possible to increase the restoring force of the outer projections 36 generated when the male connector 40 is inserted into the valve body 22 to improve the restorability of the valve body 22 to a state in which the slits 32, 33 are closed while reducing the width dimension of each of the pair of outer projections 36 along the circumferential direction of the inner projection 35 to maintain the insertability of the male connector 40 into the valve body 22.

It is needless to say that the disclosure herein is not limited to the above-described exemplary embodiment and various modifications may be made without departing from the subject matter of the invention.

For example, in the above embodiment, the cylindrical section is configured as the insertion body 23 which is formed as a separate body from the connector main body 10. However, the cylindrical section is not limited to this configuration and may be integrally formed with the connector main body 10.

Although, in the above embodiment, the outer faces 36a of the pair of outer projections 36 abut against the inner peripheral face 23b of the insertion body 23, a gap may be formed between each of the outer faces 36a of the pair of outer projections 36 and the inner peripheral face 23b of the insertion body 23. Also in this case, the stability of the valve body 22 with respect to the insertion body 23 can be improved compared to a case in which only the inner projection 35 is formed on the bottom face 30b of the valve main body 30.

Although, in the above embodiment, the outer faces 36a of the pair of outer projections 36 are inclined, these outer faces 36a may be formed with uninclined faces, that is, faces parallel to the axis of the inner projection 35.

Although, in the above embodiment, the projecting height of the pair of outer projections 36 from the bottom face 30b is larger than the projecting height of the inner projection 35 from the bottom face 30b, these projection heights may be equal to each other. When the pair of outer projections 36 is arranged on the inner side of the insertion body 23, the projecting height of the pair of outer projections 36 from the bottom face 30b may also be made smaller than the projecting height of the inner projection 35 from the bottom face 30b.

Although, in the above embodiment, the cap 21 having the connection hole 21c is used as the fixation member, the fixation member is not limited thereto. The fixation member may have another form as long as it is capable of fixing the valve body 22 to the tip of the insertion body (cylindrical section) 23.

Although, in the above embodiment, the pair of outer projections 36 are arranged along the longitudinal direction of the slits 32, 33, the positions thereof may be modified to any position.

The detailed description above describes a connector. The disclosure is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A connector comprising:
a connector main body having a flow path;
a cylindrical section having an axial end that serves as a connection opening for the flow path;
a valve body formed of an elastic body and arranged on the axial end of the cylindrical section to block the connection opening; and
a fixation member holding the valve body together with the cylindrical section, wherein
the valve body includes:
a valve main body having a slit,
an inner projection formed in an annular shape having an outer diameter smaller than an inner diameter of the cylindrical section, the inner projection projecting from a bottom face of the valve main body, and
a pair of outer projections, each formed in a circular arc shape and arranged point-symmetrically to each other with respect to an axis of the inner projection, each of the pair of outer projections projecting from the bottom face on an outer side in a radial direction with respect to the inner projection and being arranged on an inner side of the cylindrical section.

2. The connector according to claim 1, wherein the pair of outer projections are arranged along a longitudinal direction of the slit.

3. The connector according to claim 1, wherein each of the pair of outer projections includes an outer face, the outer faces facing outward in the radial direction, and wherein the outer faces are inclined in a direction approaching the axis of the inner projection as separating from the bottom face.

4. The connector according to claim 3, wherein the outer faces of the pair of outer projections contact an inner peripheral face of the cylindrical section.

5. The connector according to claim 1, wherein a projecting height of the pair of outer projections from the bottom face is larger than a projecting height of the inner projection from the bottom face.

6. The connector according to claim 1, wherein the connector main body includes a main body section and a pair of connection sections projecting outward in a radial direction from the main body section.

7. The connector according to claim 6, wherein an opening end of one of the pair of connection sections defines an inflow port to the flow path and an opening end of an other one of the pair of connection sections defines an outflow port of the flow path.

8. The connector according to claim 6, wherein the main body section includes an opening hole, the fixation member defined by the valve body and the cylindrical section forming a cap assembly which covers the opening hole in the main body section.

9. The connector according to claim 1, wherein the slit is formed on an upper face of the valve main body.

10. The connector according to claim 9, wherein the valve main body further includes a depression on the bottom face of the valve main body, the bottom face of the valve main body facing the flow path.

11. The connector according to claim 10, wherein the inner projection surrounds the depression.

12. The connector according to claim 10, wherein a partition wall is defined between the slit and the depression.

13. The connector according to claim 1, wherein the inner projection and the pair of outer projections are integrally formed with the bottom face of the valve main body.

14. The connector according to claim 1, wherein a gap in the radial direction is defined between an inner peripheral face of the cylindrical section and an outer peripheral face of the inner projection.

15. An infusion line comprising:
an infusion solution bag which store a liquid;
an indwelling needle configured to be inserted into a vein of a patient;
a clamp disposed between the infusion solution bag and the indwelling needle;
a medical tube connecting the infusion solution bag, the indwelling needle and the clamp such that the liquid in the infusion solution bad can be delivered to the vein of the patient; and
a connector according to claim 1, the connector enabling a further member to be connected to the infusion line.

16. The infusion line according to claim 15, wherein the further member to be connected comprises a syringe.

17. The infusion line according to claim 15, wherein the further member to be connected includes a male connector, the valve body being elastically deformed when the male connector is inserted into the valve body.

18. The infusion line according to claim 17, wherein the pair of outer projections elastically deform together with the valve body when the male connector is inserted into the valve body.

19. An infusion line comprising:
an infusion solution bag which store a liquid;
an indwelling needle configured to be inserted into a vein of a patient;
a clamp disposed between the infusion solution bag and the indwelling needle;
a medical tube connecting the infusion solution bag, the indwelling needle and the clamp such that the liquid in the infusion solution bad can be delivered to the vein of the patient; and
a connector comprising:
a connector main body having a flow path;
a cylindrical section having an axial end that serves as a connection opening for the flow path;
a valve body formed of an elastic body and arranged on the axial end of the cylindrical section to block the connection opening; and
a fixation member holding the valve body together with the cylindrical section, wherein
the valve body includes:
a valve main body having a slit,
an inner projection formed in an annular shape having an outer diameter smaller than an inner diameter of the cylindrical section, the inner projection projecting from a bottom face of the valve main body, and
a pair of outer projections arranged point-symmetrically to each other with respect to an axis of the inner projection, each of the pair of outer projections projecting from the bottom face on an outer side in a radial direction with respect to the inner projection and being arranged on an inner side of the cylindrical section;
the connector enabling a further member to be connected to the infusion line.

20. The infusion line according to claim 19, wherein the further member to be connected includes a male connector, the valve body being elastically deformed when the male connector is inserted into the valve body.

* * * * *